(12) United States Patent
Kaneko et al.

(10) Patent No.: US 6,409,922 B1
(45) Date of Patent: Jun. 25, 2002

(54) CHROMATOGRAPHIC SEPARATION PROCESS AND CHROMATOGRAPHIC SEPARATOR

(75) Inventors: Kikuzo Kaneko; Takayuki Masuda; Fumihiko Matsuda; Kohei Sato; Kouji Tanikawa, all of Tokyo (JP)

(73) Assignee: Organo Corporation, Tokyo (JP)

( * ) Notice: Subject to any disclaimer, the term of this patent is extended or adjusted under 35 U.S.C. 154(b) by 0 days.

(21) Appl. No.: 09/367,522

(22) PCT Filed: Dec. 24, 1998

(86) PCT No.: PCT/JP98/05842

§ 371 (c)(1),
(2), (4) Date: Aug. 16, 1999

(87) PCT Pub. No.: WO99/33540

PCT Pub. Date: Jul. 8, 1999

(30) Foreign Application Priority Data

Dec. 25, 1997 (JP) .............................................. 9-366256

(51) Int. Cl.[7] .............................................. B01D 15/08
(52) U.S. Cl. ..................... 210/659; 210/198.2; 127/46.2
(58) Field of Search ................................. 210/659, 656, 210/198.2, 635; 127/46.2

(56) References Cited

U.S. PATENT DOCUMENTS 5,127,957 A 7/1992 Heikki et al. ................ 210/656
5,556,546 A 9/1996 Masatake et al. ......... 210/198.2

FOREIGN PATENT DOCUMENTS

WO WO 95 29002 A 11/1995 .............. 210/198.2

OTHER PUBLICATIONS

Patent Abstracts of Japan, vol. 013, No. 286 (C–613), Jun. 29, 1989 & JP 01 080409 A (Japan Organo Co Ltd), Mar. 27, 1989.
Patent Abstracts of Japan, vol. 014, No. 342 (C–0743), Jul. 24, 1990 & JP 02 124895 A (Morinaga Milk Ind Co Ltd; Others: 01), May 14, 1990.

*Primary Examiner*—Ernest G. Therkorn
(74) *Attorney, Agent, or Firm*—Norris McLaughlin & Marcus

(57) ABSTRACT

In chromatographic separation in a plurality of steps with a chromatographic separator packed with an ion exchanger used as at least part of chromatographic packing, at least part of the ionic form of at least part of the ion exchanger is changed to an ionic form fit for separation of components to be separated in each step to effect chromatographic separation, whereby a starting fluid material containing at least 3 components can be efficiently separated into at least 3 fractions. A preferred example of the chromatographic separator comprising a group of packing bed units linked in endless series to form a circulation flow path is provided with a shutoff valve at a position of the circulation flow path; starting fluid material feed means, desorbent feed means and 2-fraction withdrawal means for all the packing bed units; and a single-fraction withdrawal means connected to the circulation flow path on the upstream side of the shutoff valve and without any packing bed unit therebetween.

2 Claims, 2 Drawing Sheets

CHROMATOGRAPHIC SEPARATION PROCESS AND CHROMATOGRAPHIC SEPARATOR

REFERENCE TO RELATED APPLICATIONS

This application is a 371 of PCT/JP98/05842 filed Dec. 24, 1998.

1. Technical Field

The present invention relates to a chromatographic separation process and a chromatographic separator, and more particularly to a chromatographic separation process for separating a starting fluid material containing at least 3 components into at least 3 fractions in a plurality of steps with a chromatographic separator packed with an ion exchanger as at least part of chromatographic packing and a chromatographic separator not only effectively usable for the above-mentioned chromatographic separation process but also usable for a variety of other processes.

2. Background Art

There are various conventional methods of chromatographic separation of a starting fluid material containing at least 3 components into the respective components, representative examples of which include the following methods:

A method (1) is a batchwise one wherein analytical high-performance liquid chromatography is scaled up, and which is generally called preparatory chromatography.

A method (2) is one using either 2 simulated moving bed chromatographic separators for separation of only 2 components or using such a chromatographic separator twice as disclosed in Japanese Patent Laid-Open No. 124,895/1990. More specifically, a starting material is either first separated into a component A and a mixture of components B+C, followed by separation of the mixture of components B+C into the components B and C, or first separated into a mixture of components A+B and the component C, followed by separation of the mixture of components A+B into the components A and B. This is so because separation of only 2 components is possible with an ordinary simulated moving bed chromatographic separator. Thus, in order to actually separate 3 components from one another, either 2 simulated moving bed chromatographic separators must be prepared or one such separator must be used twice. In the latter case, a solution midway of separation (fraction of mixture) must be stored once, and then subjected to separation under varied conditions while using the same separator again.

A method (3) is one disclosed in Japanese Patent Laid-Open No. 227,804/1992, wherein one improved simulated moving bed chromatographic separator packed with one packing is used to efficiently and continuously separate a fluid mixture containing at least 3 components into fractions enriched with the respective components. Herein, the term "enriched with components" refers to solids-based concentration (enrichment) of components to be separated (components desired to be separated) in the respective fractions separated in the direction of fluid flow. Thus, the degree of enrichment is correlated with purity and recovery.

A method (4) is one disclosed in Japanese Patent Laid-Open No. 80,409/1989, wherein separation columns (packed column units having packing bed units) packed with a first packing having the following partition coefficients for components: component A<component B<component C are arrayed alternately and used together with separation columns packed with a second packing having the following partition coefficients for components: component A<component C<component B.

The methods (2), (3) and (4) are fundamentally those whereto application is made either of a basic simulated moving bed procedure comprising an operation of feeding a starting fluid material containing a plurality of components to be separated and desorbent (called "eluent" in the case of liquid) at respective designated positions to an endless circulation system (loop) made up of a plurality of packing bed units packed with chromatographic packing (sorbent) and linked endlessly to flow the starting fluid material and the desorbent in one direction through the endless circulation system, and withdrawing fractions from zones enriched with respective components out of the endless circulation system while taking advantage of a phenomenon that a plurality of components to be separated are separated into respective zones enriched with the respective components due to a difference between the components in affinity for chromatographic packing, and an operation of intermittently displacing the starting fluid material and desorbent feed positions as well as the fraction withdrawal positions in the direction of fluid flow as if the chromatographic packing were apparently moved in the direction opposite to that of fluid flow, whereby two fractions enriched with the respective components are continuously obtained from the starting fluid material; or of an improved or altered procedure based on the basic simulated moving bed procedure (in the present invention, the "simulated moving bed procedure" is defined as encompassing such improved or altered ones as well).

Although the foregoing methods all belong to the same technology in respect of chromatographic separation of a starting fluid material containing at least 3 components into at least 3 fractions, they involve the following respective demerits when they are adopted in industrial-scale equipment for carrying out the separation technology.

The method (1) is poor in separation because it is batchwise, and is often unfit for industrial-scale separation involving treatment of a large amount of starting liquid material because the amount of eluent to be used must inevitably be large.

The method (2) requires either installing 2 simulated moving bed chromatographic separators or using the same separator twice. Where 2 simulated moving bed chromatographic separators are installed, the equipment cost is increased. Where the same separator is used twice, the same packing must inevitably be used because replacing chromatographic packing every time is troublesome in an aspect of operation. This involves a problem that all 3 components cannot efficiently be separated from one another in some cases because one kind of packing is used. For example, there arises a case where a component A is too well separated from a component B, but separation of the component B from a component C is so poor that it is difficult to heighten the component purities of all fractions.

The method (3) also sometimes fails in efficient and distinct separation of all 3 components because one kind of packing is used. For example, there arises a case where a component A is too well separated from a component B, but separation of the component B from a component C is so poor that it is difficult to heighten the component purities of all fractions.

The method (4) involves a difficulty in combining 2 kinds of suitable packings for a starting solution to be subjected to chromatographic separation.

Accordingly, in the foregoing methods (2), (3) and (4), the separability of components [relevant to the load (feed rate) of a starting fluid material], the purities and recoveries of components contained as objects of separation in recovered fractions, the amount of used desorbent relevant to concentration energy involved in concentrating recovered fractions (relevant to the desired component concentrations of the recovered fractions), etc. are influenced by packing(s) packed in packing bed units, while involving a problem that a countermeasure for an improvement in respect of one of those influences tends to produce other adverse effects.

Although it can be said that choice and use of the optimum packing capable of suitably adjusting the foregoing various influences will suffice in order to solve such a problem, choice of the optimum packing is not easy as a matter of fact. For example, when the resolution, by packing, of components contained in a starting fluid material is enhanced as much as possible in order to heighten the purities and recoveries of components as objects of recovery, intervals between a plurality of zones enriched with respective components are spread too broad in the endless circulation system, whereby the amount of desorbent to be used is increased (the amount of desorbent to be used for desorption of a strong-affinity component in particular is increased because of a large difference between components in affinity for packing), leading to a problem that the component concentrations of respective recovered fractions are lowered. On the other hand, using chromatographic packing poor in resolution for the purpose of decreasing the amount of desorbent to be used involves a problem that the purities and recoveries of components are lowered. Thus, the chances are rare that there exists any conventional packing suitable in respect of the resolution of a plurality of components to be separated, and creation of such a packing is not easy. Incidentally, the term "resolution," which is a yardstick indicative of the extent of separation of 2 components, is defined as being equal to a value found by dividing the distance between the centers of two adjacent enriched zones (bands) 1 and 2 by an average band width (see "High-Performance Liquid Chromatography" published by Tokyo Kagaku Dozin Co., Ltd. in 1976).

An object of the present invention, which has been made in view of the foregoing problems of the prior art technologies, is to provide a process for efficient chromatographic separation of components from a starting fluid material containing at least 3 components.

Another object of the present invention is to provide a chromatographic separator having a possibility of service in a wide variety of processes in addition to effective service to the above-mentioned process.

DISCLOSURE OF THE INVENTION

As a result of extensive investigations on the foregoing conventional is methods, the inventors of the present invention have solved the problems of the conventional chromatographic separation methods to complete the present invention. According to the present invention, for example, there can simultaneously be satisfied antinomic requirements that high purities and high recoveries of components as objects of separation be secured, and that the components be obtained while securing as high their concentrations as possible.

The chromatographic separation process of the present invention is characterized in that chromatographic separation is effected while changing at least part (based on ion exchange capacity) of the ionic form of part or the whole of an ion exchanger to an ionic form capable of increasing the resolution of components to be separated in each step in chromatographic separation for separating a starting fluid material containing at least 3 components into at least 3 fractions in at least 2 steps with a chromatographic separator packed with the ion exchanger as at least part of chromatographic packing (sorbent).

More specifically, the present invention provides a chromatographic separation process for separating a starting fluid material containing at least 3 components into at least 3 fractions in a plurality of steps with a chromatographic separator packed with an ion exchanger; characterized in that chromatographic separation is effected while changing at least part (based on ion exchange capacity) of the ionic form of part or the whole of the ion exchanger used as at least part of chromatographic packing (sorbent) to an ionic form fit for separation of components to be separated in each step. In the process of the present invention, use is preferably made of a chromatographic separator comprising a plurality of packing bed units packed with the ion exchanger as at least part of chromatographic packing, in which separator at least the position of feeding desorbent is intermittently displaced in the direction of fluid flow.

The present invention also provides a chromatographic separator comprising a system of a group of packing bed units packed with sorbent and linked in endless series to form a circulation flow path, in at least one position (shutoff/opening position) of which an interchange can be made between a state wherein internal fluid is endlessly circulated through the circulation flow path while allowing fluid to be fed into and withdrawn out of the system and a state wherein internal fluid flow is shut off while allowing fluid to be fed into and withdrawn out of the system; characterized by comprising a starting fluid feed means and a desorbent feed means connected to the circulation flow path between every adjacent packing bed units of the group of the packing bed units, 2-fluid withdrawal means connected to the circulation flow path between every adjacent packing bed units of the group of the packing bed units for respectively withdrawing 2 fluid fractions, and one or two fluid withdrawal means connected to the circulation flow path and disposed on the upstream side of said at least one position (shutoff/opening position) with no and/or one packing bed unit therebetween for withdrawing another fluid fraction.

The process of the present invention is not always limited to a case where only one kind of ion exchanger is used as the ion exchanger serving as at least part of chromatographic packing. As proposed by the instant applicant in Japanese Patent Application No. 9-257055 (i.e., 257,055/1997), the process of the present invention can also be applied to a case where the aforementioned resolution is adjusted by taking advantage of a coexistent state of at least 2 different packings selected from among those differing in the resolution of components to be separated which are contained in a starting fluid material, i.e., a case where said at least 2 different packings are used in a mixed state and/or a multi-layer stratified state and/or a coexistent state of said at least 2 different packings being used but, for example, only one packing among said at least 2 different packings being used in one or a plurality of packing bed units among a group of packing bed units endlessly linked In this case, the purpose of the present invention may be attained if only at least one packing among said at least 2 different packings is an ion exchanger. Ion exchange resins, zeolite, and the like can be used as the ion exchanger. Herein, the term "differing in the resolution" refers to involving a difference of at least 0.1, preferably at least 0.2, between 2 packings in the resolution of 2 components to be separated from each other when that resolution is measured under actual separation conditions (temperature, flow velocity, etc.) for the 2 packings packed in respective test columns having the same shape, for example, at a standard packing bed height (e.g., 0.3- to 1-fold height of actual bed height of packed column unit). Where said at least 2 different packings are used in a coexistent state, examples of packing usable in combination with the ion exchanger include silica gel, activated carbon, and other natural or synthetic sorbents. The ratio, kinds, etc. of those packings can be chosen in accordance with the kinds of components to be separated, the purpose, etc. on the basis of various experimental results.

Since a smaller amount of a reagent for changing the ionic form of the ion exchanger is advantageous in aspects of expense, time, etc., it is preferred either to change the ionic form of the ion exchanger in an irreducible minimum amount or to change the ionic form of the ion exchanger at an irreducible minimum proportion ("changed ionic form/ whole ionic form ratio" based on the ion exchange capacity of the ion exchanger) even if the ionic form of the whole ion exchanger is changed. The term "changing the ionic form" will hereinafter be defined as encompassing all such cases.

The process of the present invention may be carried out either according to a batchwise preparatory chromatographic separation procedure or according to a simulated moving bed chromatographic separation procedure. Accordingly, not only a wide variety of chromatographic separators such as a batchwise preparatory chromatographic separator, a basic simulated moving bed chromatographic separator and a simulated moving bed chromatographic separator for separation of 3 components as are used in the foregoing conventional methods but also a wide variety of improved or simplified chromatographic separators derived therefrom can be used as such in the process of the present invention. A batchwise preparatory chromatographic separator usually includes one bed, which is a packing bed packed with an ion exchanger in a column wherein the ionic form of the ion exchanger is changed in each step, but may alternatively be constructed in such a way that it includes, for example, two stratified beds differing in the ionic form of an ion exchanger in a column wherein a starting fluid material is flowed from the upstream end of the first bed and a first eluting (outflowing) fraction of mixture A+B from the first bed due to subsequent feed of desorbent is passed as such through the second bed to separately withdraw fractions A and B from the downstream end of the packed column (separation column) while withdrawing a fraction C from a position at the boundary between the first and second beds, whereby two steps with a change in the ionic form of the ion exchanger therebetween can be continuously taken in the batchwise separator. In the latter case, the separator may be constructed in such a way that a desorbent feed inlet is also provided at a position at the boundary between the first and second beds, or that a plurality of withdrawal outlets capable of switching the boundary between the first and second beds, for example, by changing the ionic form of the ion exchanger in the second bed, if necessary, through reverse utilization of the withdrawal outlets are provided favorably to enable the separator to cope with various operating conditions and various starting fluid materials. In a simulated moving bed chromatographic separator comprising a plurality of packing bed units (packed column units) packed with an ion exchanger as will be described later, a change in the ionic form of the ion exchanger in each step may be made either in such a manner that the ionic form of the ion exchanger in all the packing bed units is changed, or in such a manner that the ionic form of the ion exchanger in at least one packing bed unit is changed mostly to enable the purpose of the a present invention to be still attained. In this case, a packing other than ion exchanger may be used in combination with the ion exchanger as already described, and it is a matter of course that a packing other than ion exchanger may be used in all of at least one packing bed unit in so far as both are used in combination.

Reagents usable in changing the ionic form of, e.g., a cation exchanger as the ion exchanger include various acids; salts and hydroxides of alkali metals such as sodium and potassium as well as ammonium, and mixtures thereof, which can change the ionic form to a monovalent ion form; salts and hydroxides of alkaline earth metals such as calcium and magnesium, and mixtures thereof, which can change the ionic form to a bivalent ion form; and other reagents such as aluminum chloride, which can change the ionic form to a trivalent ion form or the like. A proper reagent may be chosen in connection with components to be separated.

For example, when a simulated moving bed chromatographic separator is used, a method wherein a solution of a salt, an acid or an alkali in an aqueous medium is flowed through at least one packing bed unit (packed column unit) is simple and convenient as the method of changing the ionic form of the ion exchanger. Alternatively, the ion exchanger such as an ion exchange resin may be transferred to a separate preparatory column and changed in the ionic form thereof in that column. From the standpoint of actual operation, a substantially neutral solution of a salt in an aqueous medium is preferably used rather than an acidic or alkaline aqueous solution.

For example, a gel type strongly acidic cation exchange resin is used for separation of saccharides. According to empirical laws, a monovalent ion form is so suitable for separation of monosaccharides, disaccharides, trisaccharides, etc. differing in molecular weight from one another that an aqueous solution of a salt such as sodium chloride is desirably flowed in contact with the ion exchanger to increase the amount of the monovalent ion form, while a bivalent ion form is so suitable for mutual separation of saccharides having the same molecular weight that an aqueous solution of a salt such as calcium chloride is desirably flowed in contact with the ion exchanger to increase the amount of the bivalent ion form. The process of the present invention is preferably carried out under such conditions that the ionic form composition of the ion exchanger is not substantially varied in keeping with the progress of separation operation in order to maintain the resolution constant. For example, in separation of saccharides with use of an ion exchange resin, however, either a case where the ionic form thereof goes in such a direction as to approach the ionic form composition equilibrated with various kinds of ions contained in a starting solution material or a case where some ions of the ion exchange resin in a certain packing bed (e.g., a packed column unit) move to a next packing bed may arise in keeping with progress of operation. Even in such a case, however, no problems arise in so far as there exists an amount of the ionic forms; A necessary for separation per total amount of the ion exchange resin in the whole packing bed.

A generic and simple description will now be made of an example of the basic simulated moving bed chromatographic separator that can be used in the chromatographic separation process of the present invention. Incidentally, although a case where a liquid containing at least 3 components is dealt with as the starting fluid material will mainly be described in order to simplify the description of the process of the present invention, it goes without saying that the process of the present invention is applicable to gases containing at least 3 components. This separator comprises a system comprising a plurality of packing bed units linked in endless series and packed with solid sorbent (comprising at least ion exchanger in the present invention), a means for circulating internal fluid in one direction in the system, a starting fluid material feed means for choosing any one of the packing bed units and feeding thereto a starting fluid material, a desorbent feed means for choosing any other one of the packing bed units and feeding thereto desorbent (also called "eluent" in the case of liquid), a first fluid withdrawal means for choosing any one of the packing bed units and withdrawing therefrom a fraction A (e.g., raffinate) out of the system, a second fluid withdrawal means for choosing any other one of the packing bed units and withdrawing therefrom a fraction C (e.g., extract) out of the system, and a switching control means for sequentially displacing the fluid feed positions and the fluid withdrawal positions in the downstream direction of fluid flow in the system while maintaining the relationship between the fluid feed positions and the fluid withdrawal positions in the system.

A generic and simple description will now be made of an example of a simulated moving bed chromatographic separation process using this simulated moving bed chromatographic separator. The group of the packing bed units linked in endless series is regarded as being divided into first, second, third and fourth sections in the downstream direction of fluid flow when viewed from the desorbent feed position. Desorbent such as eluent is fed via a feed valve to circulating fluid at the inlet of a packing bed unit positioned foremost in the first section and the fraction C large in the amount of a sorbed component, such as extract, is withdrawn via a withdrawal valve from circulating fluid at the outlet of a packing bed unit positioned rearmost in the first section, while a starting fluid material is fed via a feed valve to circulating fluid at the inlet of a packing bed unit positioned foremost in the third section and the fraction A small in the amount of the sorbed component, such as raffinate, is withdrawn via a withdrawal valve from circulating fluid at the outlet of a packing bed unit positioned rearmost in the third section. The desorbent feed position, the fraction C withdrawal position, the starting fluid material feed position, and the fraction A withdrawal position are each operationally displaced one by one in the downstream direction in keeping with the movement of a zone wherein the component in the starting fluid material is sorbed on sorbent. According to the present invention, such a simulated moving bed chromatographic separation process is carried out in a plurality of steps in each of which the ionic form of an ion exchanger used in the process is changed, whereby the starting fluid material containing at least 3 components can be separated into at least 3 fractions. However, simulated moving bed chromatographic separation processes include various improved or altered methods, examples of which include a method wherein the starting fluid material feed position is fixed (see Japanese Patent Laid-Open No. 132,586/1997), and a method wherein the position of withdrawing a certain fraction is fixed (see Japanese Patent Laid-Open No. 132,586/1997).

MODES FOR CARRYING OUT THE INVENTION

Modes for carrying out the present invention will now be described while referring to the accompanying drawings, but should not be construed as limiting the scope of the present invention unless they depart from the subject matter of the present invention.

Figure 1:
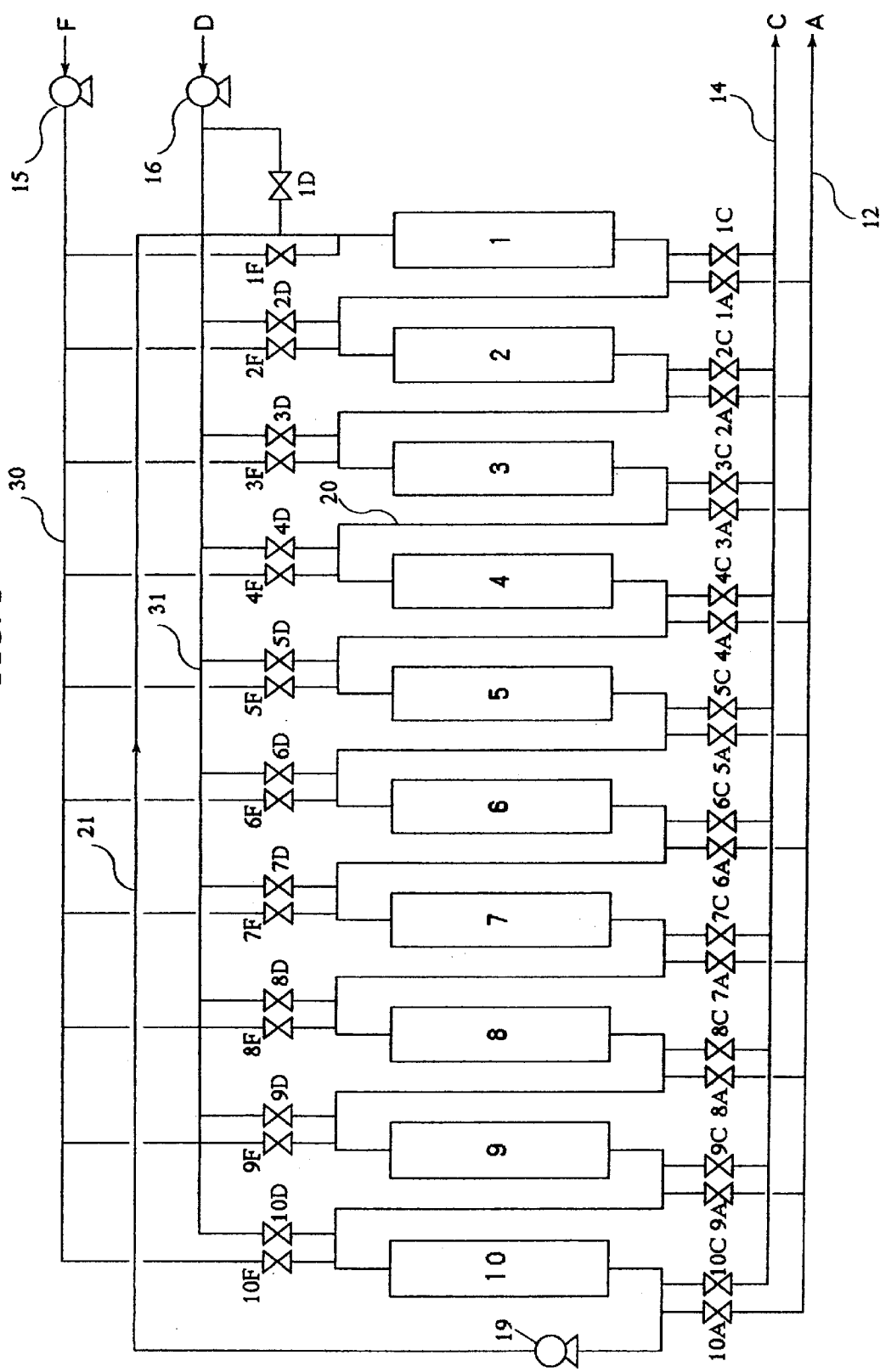
FIG. 1 is a schematic illustration of an example of the constitution of a simulated moving bed chromatographic separator that may be used for carrying out the process of the present invention.

FIG. 1 is a schematic illustration of an example of the constitution of a simulated moving bed chromatographic separator that may be used for carrying out the process of the present invention. This separator is a specific example of the aforementioned basic simulated moving bed chromatographic separator. In FIG. 1, numerals 1 to 10 refer to packing bed units (packed column units), 1A to 10A to fraction A withdrawal valves, 1C to 10C to fraction C withdrawal valves, 1D to 10D to desorbent feed valves, 1F to 10F to starting fluid material feed valves, A to fluid of fraction A such as raffinate, C to fluid of fraction C such as extract, D to desorbent such as eluent, F to starting fluid material, 12 to a fraction A withdrawal piping, 14 to a fraction C withdrawal piping, 15 to a starting fluid material feed pump, 16 to a desorbent feed pump, 19 to a circulating pump, 20 and 21 to connecting pipings, 30 to a starting fluid material feed piping, and 31 to a desorbent feed piping.

The ends of the packing bed units 1 to 10 are endlessly linked with the tops of the respective next packing bed units by means of the connecting pipings 20 and 21. The fraction A withdrawal valves 1A to 10A and the fraction C withdrawal valves 1C to 10C are connected to the connecting pipings on the downstream sides of the respective packing bed unit, while connecting the connecting pipings with branch pipes having the respective starting fluid material feed valves 1F to 10F and branched from the starting fluid material feed piping 30 for the starting fluid material being fed by the starting fluid material feed pump 15, and with branch pipes having the respective desorbent feed valves 1D to 10D and branched from the desorbent feed piping 31 for the desorbent being fed by the desorbent feed pump 16 on the upstream side of the respective packing bed units. The circulating pump 19 is connected to the middle of the piping 21 extended from the end of the packing bed unit 10 to the top of the packing bed unit 1. The fraction A withdrawal valves 1A to 10A are connected to the fraction A withdrawal piping 12, while the fraction C withdrawal valves 1C to 10C are connected to the fraction C withdrawal piping 14. Incidentally, the circulating pump 19, which is installed in the middle of the piping 21, is capable of controlling the flow rate to any set points in accordance with a flow rate sequence program with the aid of a controller not shown in the figure. This circulating pump 19 may be installed between any mutually adjacent packing bed units, and whatever number of circulating pumps of this kind may be provided if necessary. Further, the feed valves and the withdrawal valves are each controlled to be opened or closed in accordance with a predetermined valve 4 opening and closing sequence program by means of the controller not shown in the figure. Although the number of packing bed units is 10 in FIG. 1, it is not limited thereto.

A description will now be made of the running operations of the simulated moving bed chromatographic separator of FIG. 1. In Stage 1, for example, the starting fluid material feed valve 6F is opened to feed the starting fluid material via the top of the packing bed unit 6 and the desorbent feed valve 1D is opened to feed desorbent via the top of the packing bed unit 1 while introducing fluid from the end of the packing bed unit 10 into the top of the packing bed unit 1 via the circulating pump 19. Since this separates fluid into a fraction enriched with a component having a weak affinity for chromatographic packing (fraction A) and a fraction enriched with a component having a strong affinity therefor (fraction C) in the direction of circulating flow, the fraction C withdrawal valve 2C is opened to withdraw the fraction C from the end of the packing bed unit 2 and the fraction A withdrawal valve 8A is opened to withdraw the fraction A from the end of the packing bed unit 8.

Accordingly, in Stage 1 in this case, a first section ranging from the desorbent feed inlet to the fraction C withdrawal outlet involves 2 packing bed units, a second section ranging from the fraction C withdrawal outlet to the starting fluid material feed inlet involves 3 packing bed units, a third section ranging from the starting fluid material feed inlet to the fraction A withdrawal outlet involves 3 packing bed units, and a fourth section ranging from the fraction A withdrawal outlet to the desorbent feed inlet involves 2 packing bed units. Needless to say, however, the present invention is not limited to the mode of this case.

In Stage 2 after the lapse of predetermined time, the desorbent feed valve 1D opened in Stage 1 is closed and the desorbent feed valve 2D is instead opened, while the opened fraction C withdrawal valve is displaced from 2C to 3C, the opened starting fluid material feed valve from 6F to 7F, and the opened fraction A withdrawal valve from 8A to 9A in the same manner as described just above.

Stages 3 to 10 of chromatographic separation are performed according to the foregoing operation of sequentially displacing every one of the opened valves by one packing bed unit on the downstream side in the direction of circulating flow every stage. Such switching of valves results in performing an operation which apparently looks as if it moved the chromatographic packing (sorbent) in the direction opposite to that of circulating flow.

Figure 2:
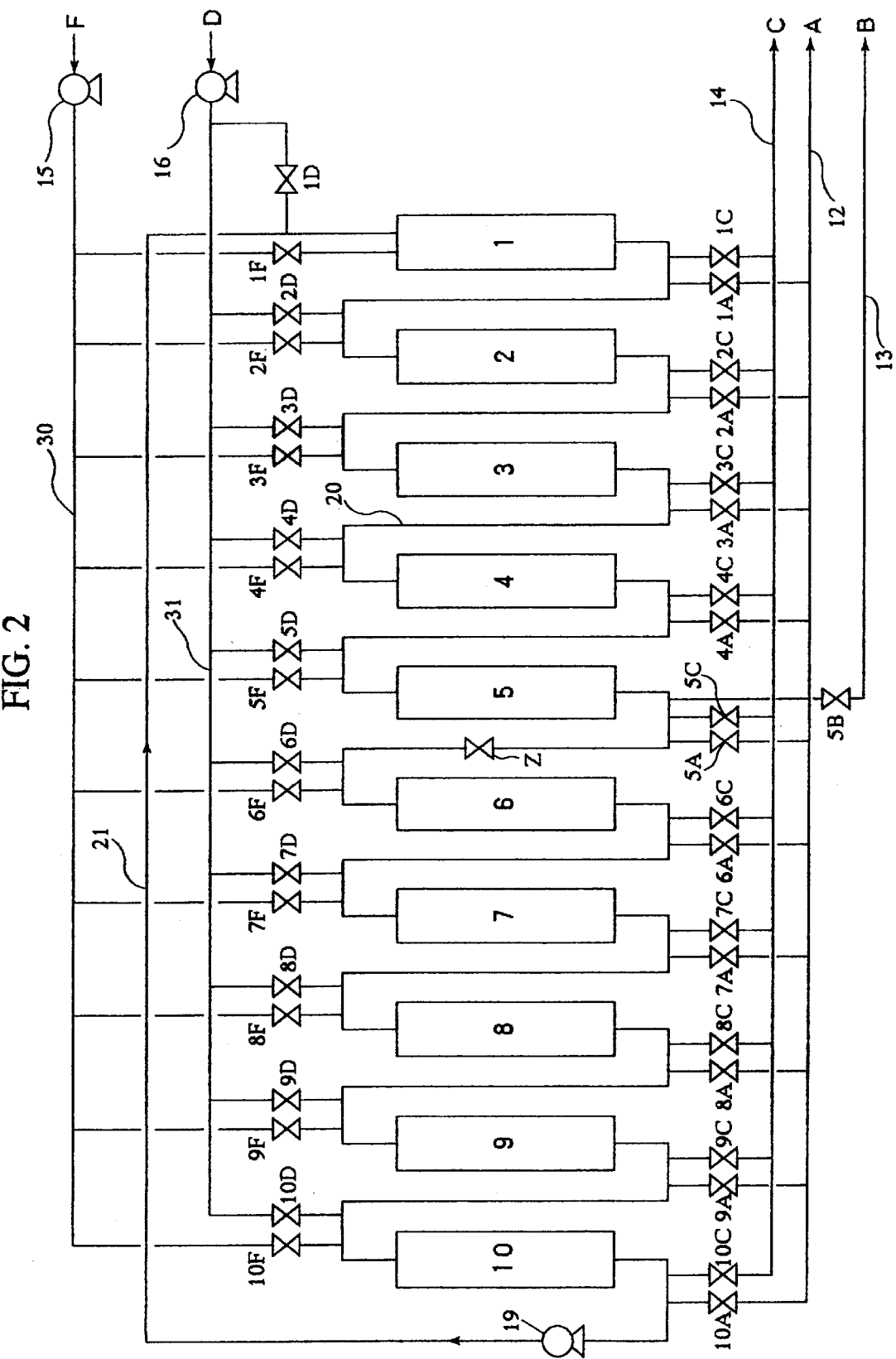
FIG. 2 is a schematic illustration of an example of the constitution of the simulated moving bed chromatographic separator of the present invention that may be used for carrying out the process of the present invention and has an applicability to a variety of processes.

FIG. 2 is a schematic illustration of a specific example of the constitution of the improved simulated moving bed chromatographic separator of the present invention that may be used for carrying out the process of the present invention. This separator, which was used in the following Examples and Comparative Examples, is such one improved over the separator shown in FIG. 2 in Japanese Patent laid-Open No. 132,586/1997 (the starting solution feed position is fixed) that it can be run not only in the same manner as disclosed in Japanese Patent laid-Open No. 132,586/1997 but also substantially in the same manner as the foregoing separator of FIG. 1 (the starting solution feed position is not fixed). Accordingly, symbols in FIG. 2, which correspond to those in FIG. 1, are the same as in FIG. 1. Thus, FIG. 2 is different from FIG. 1 in that there are additionally drawn a fraction B withdrawal valve 5B, a shutoff valve Z, fluid of fraction B, and fraction B withdrawal piping 13 in FIG. 2. Incidentally, the fraction B withdrawal piping 13 with the fraction B withdrawal valve 5B may be connected with a connecting piping 20 between packing bed units 4 and 5 instead of between packing bed units 5 and 6. Alternatively, it may be branched in such a way that it is connected with the connecting pipe 20 between the packing bed units 4 and 5 and between the packing bed units 5 and 6, provided that branch pipes are provided with respective fraction B withdrawal valves. In the latter case, one of the two fraction B withdrawal valves is usually opened during withdrawal of the fraction B.

The shutoff valve Z provided between the packing bed units 5 and 6, the number of which is not necessarily limited to one, is controlled to be opened or closed by a controller not shown in the figure. Two or more such shutoff valves may alternatively be provided at different positions in the circulation flow path according to the purpose.

Where a starting fluid material containing at least 2 components is separated into 2 fractions using the separator of FIG. 2 in one step, the constitution of the separator of FIG. 2, which is in a state wherein the shutoff valve Z remains opened and the fraction B withdrawal valve 5B remains closed, can be regarded as being substantially the same as the constitution of the separator of FIG. 1. In this case, therefore, the procedure of operating the separator of FIG. 2 is, for example, the same as described in connection with the procedure of operating the separator of FIG. 1. Accordingly, the explanation of the procedure of operating the separator of FIG. 2 in this case is omitted (see the description of the procedure of operating the separator of FIG. 1).

A description will now be made of a case where a starting fluid material containing at least 3 components (components A, B and C) is separated into 3 fractions enriched with respective components using the separator of FIG. 2 in one step (this one step usually comprises 2 substeps as is understandable by reference to a case where such substeps are taken in Step 1 of the following Example 2) while effectively making the most of the shutoff valve Z. In this case, the affinities of the components for chromatographic packing (comprising at least ion exchanger in the process of the present invention) are in the following order: component C>component B>component A.

In Substep 1-1, while in a state wherein the shutoff valve Z is closed and a starting fluid material feed valve 6F is opened, the starting fluid material F is fed via the top of the packing bed unit 6 wherein a sorption zone enriched with the component A is formed, and a fraction A is withdrawn from the end of a packing bed unit 8 on the downstream side of the starting fluid material feed position via a fraction A withdrawal valve 8A being opened, while simultaneously desorbent D is fed via a desorbent feed valve 1D being opened to the top of a packing bed unit 1 on the upstream side of the packing bed unit 5 wherein a sorption zone enriched with the component B is formed, and a fraction B is withdrawn from the end of the packing bed unit 5 via a fraction B withdrawal valve 5B being opened [see "Open Valves" in Stage 1 of Step 1 in the following Example 2 since this Stage 1 corresponds to Substep 1-1]. Incidentally, since the fraction A is withdrawn in the following Substep 1-2 as well, there may be adopted an embodiment wherein the fraction A is not withdrawn in Substep 1-1 though it depends on the affinity of the component A for chromatographic packing. Alternatively, there may be adopted an embodiment wherein a fraction C, or the fractions A and C are withdrawn in Substep 1-1 if necessary.

In Substep 1-2, the starting fluid material feed valve 6F is closed to stop feeding the starting fluid material, and the shutoff valve Z is opened. With internal fluid being circulated in the system comprising packing bed units linked in endless series, desorbent is fed to that system, and fractions of the components (fractions A and C) are withdrawn from the ends of packing bed units wherein sorption zones enriched with the respective components are formed and left in Substep 1-1, while performing an operation of sequentially displacing the desorbent feed position and the fraction withdrawal positions to those for packing bed units on the downstream side in the system in keeping with the movement of the sorption zones. How to perform such a displacement operation can be understood by reference to "Open Valves" in Stages 2 to 10 of Step 1 in the following Example 2 as a specific instance of the operation. In running an industrial-scale separator, Substeps 1-1 and 1-2 as one cycle are usually repeated. In principle, Substeps 1-1 and 1-2 should possibly be regarded as separate steps, but are considered Step 1 as a single step consisting of the two substeps as far as the process of the present invention is carried out. This is so because the ionic form of the ion exchanger used as at least part of chromatographic packing is not changed before the start of Substep 1-2.

Substep 1-1 is a step wherein the distribution of sorption zones of respective components to be withdrawn in the next cycle is formed by feeding the starting fluid material while withdrawing out of the system a fraction of the component classed as one having a medium affinity for chromatographic packing (fraction B) among fractions of components corresponding to already formed sorption zones. In this step, a large amount of the fraction B can be removed, or withdrawn, in a short time. Incidentally, since it is not desired that fluid in the system flows into the starting fluid material feed position from the upstream side thereof in this step, the shutoff valve is provided as a means for mechanically ensuring shutoff of fluid flow. Even if no shutoff valve is provided, however, fluid flow can operationally be shut off by controlling the feed rate of the starting fluid material and the withdrawal rate of the fraction B.

Substep 1-2 is a step wherein fractions enriched with respective components other than the component B are withdrawn out of the system with internal fluid being circulated in the system and without the starting fluid material being fed thereto by an operation being performed in accordance with the general simulated moving bed chromatographic separation procedure, and wherein the components of the starting fluid material fed into the system afresh in Substep 1-1 form sorption zones of the components sequentially separated and ranging from the component A (component having weak affinity for chromatographic packing, i.e., sorbent) to the component C (component having strong affinity for sorbent). The procedure of this Substep 1-2 taken in accordance with the simulated moving bed operation of withdrawing 2 fractions while feeding desorbent, though not particularly limitative, may be any conventional one except for feeding no starting fluid material, an example of which is a case where starting solution is not fed in the method particularly described on page 2, rightupper column, line 2 to left-lower column, the last line, and shown in FIG. 3 in Japanese Patent Laid-Open No. 91,205/1987 (accordingly, the second and third sections may be considered one and the same section in the instant description). Specifically, with internal fluid being circulated in the system by means of a pump or the like, an operation of sequentially displacing in the downstream direction of circulating flow the position of feeding desorbent via the top of a packing bed unit on the upstream side of a section where a sorption zone enriched with a predetermined component exists and the position of simultaneously withdrawing a fraction enriched with that component from the end of a packing bed unit on the downstream side of that section in keeping with movement of the sorption zone is performed for a plurality of components other than a component having a medium affinity for chromatographic packing (sorbent) to take Substep 1-2.

Although the procedure of repeating Substeps 1-1 and 1-2 has been described in connection with a state wherein the separator is continuously run, a preliminary step of performing only an operation of feeding the starting fluid material into the system to form sorption zones of components sequentially separated and ranging from the component having a weak (b affinity for sorbent to the component having a strong affinity for sorbent may be done in order to start up the separator before Substep 1-1.

Such Substeps 1-1 and 1-2 as one cycle are fundamentally repeated. Needless to say, however, they can be done according to a variety of altered embodiments.

For example, only the starting fluid material may be fed into the system without feeding desorbent in Substep 1-1. When the starting fluid material and desorbent are simultaneously fed in Substep 1-1 as described above, however, the feed rate of the starting fluid material and the withdrawal rate of the fraction B can be controlled (control of mass balance). Further, feeding desorbent can increase the flow velocity of internal fluid on the downstream side of the desorbent feed position, whereby the moving velocity of a predetermined component in the sorption zone thereof can be arbitrarily chosen.

EXAMPLES

The following Examples will specifically illustrate the process of the present invention in comparison with Comparative Examples, but should not be construed as limiting the scope of the process of the present invention. Incidentally, in the following Examples and Comparative Examples, the solids-based composition is expressed in terms of a real percentage in high-performance liquid chromatography using a sodium-form ion exchange column and a differential refractometer, the term "one cycle time" denotes the time required for completing all stages ranging from Stage 1 to Stage 10, and the symbol "L" stands for liter(s). Generally speaking, all stages are usually repeated continuously through a plurality of cycles as needed.

Example 1

For the purpose of separating lactulose from a crude lactulose solution (solids content: 60 wt. %; solids-based composition: 5.3% lactose, 4.9% epilactose, 78.8% lactulose, 10.0% galactose, 0.6% tagatose, 0.4% other monosaccharides) as a starting fluid material (hereinafter referred to as "starting solution"), the simulated moving bed chromatographic separator of FIG. 2 wherein packings in mutually different ionic forms were used in a coexistent state was run under the following operating conditions in order to first separate disaccharides and monosaccharides from each other in Step 1. The resolution of lactulose (main component of disaccharides) and galactose (main component of monosaccharides) by used packing was 0.32 for a first packing in the Ca form and 0.52 for a second packing in the Na form. The partition coefficient of tagatose was 0.72 for the first packing in the Ca form and 0.47 for the second packing in the Na form.

The used packings were Amberlite (registered trademark) CG-6000 (gel type strongly acidic cation exchange resin for chromatographic separation) manufactured by Rohm and Haas Company. The total amount of the packings in the 10 packing bed units was 147 L. The packing bed units 1, 2, 3, 6, 7 and 8 were packed with the packing in the Na form, while the other packing bed units 4, 5, 9 and 10 were packed with the packing in the Ca form, whereby the packings in the mutually different ionic forms were used in a coexistent state when viewed from the whole equipment.

Other operating conditions were as follows:

Packing Bed Units: 108 mm in inner diameter, 1600 mm in bed height, 10 in the number of packed column units Operating Temperature: 60° C.

One Cycle Time: 1.84 hr.

Linear Flow Velocity in Packing Bed Units between Starting Solution Inlet and Fraction C Withdrawal Outlet: 5.00 m/hr.

Feed Rate of Starting Solution: 4.12 L/hr. (0.028 L/L-packings/hr., based on packings)

Feed Rate of Eluent Water: 19.40 L/hr.

Withdrawal Rate of Fraction A: 8.53 L/hr.

Withdrawal Rate of Fraction C: 14.99 L/hr.

Eluent Water/Starting Solution (vol. ratio): 4.7

Open valves in each stage were as follows. Fed liquids and withdrawn solutions were common to all stages. Specifically, the starting solution and eluent water were fed and 2 fractions A and C were withdrawn.

| Stage 1  | 6F,  | 1D,  | 8A,  | 2C,  | Z |
|----------|------|------|------|------|---|
| Stage 2  | 7F,  | 2D,  | 9A,  | 3C,  | Z |
| Stage 3  | 8F,  | 3D,  | 10A, | 4C,  | Z |
| Stage 4  | 9F,  | 4d,  | 1A,  | 5C,  | Z |
| Stage 5  | 10F, | 5D,  | 2A,  | 6C,  | Z |
| Stage 6  | 1F,  | 6D,  | 3A,  | 7C,  | Z |
| Stage 7  | 2F,  | 7D,  | 4A,  | 8C,  | Z |
| Stage 8  | 3F,  | 8D,  | 5A,  | 9C,  | Z |
| Stage 9  | 4F,  | 9D,  | 6A,  | 10C, | Z |
| Stage 10 | 5F,  | 10D, | 7A,  | 1C,  | Z |

As a result of operation, there were obtained fractions A and C having the following respective solids contents and solids-based compositions:

|  | Fraction A | Fraction C |
|---|---|---|
| Solids Content | 300 g/L | 42 g/L |
| Lactose | 6.4% | 1.1% |
| Epilactose | 6.0% | 0.5% |
| Lactulose | 87.5% | 44.4% |
| Galactose | 0.1% | 49.1% |
| Tagatose | 0.0% | 3.0% |
| Other Monosaccharides | 0.0% | 1.9% |

Incidentally, the lactulose recovery of the fraction A was 89.3%.

The fraction A solution (solids-based composition: 6.4% lactose, 6.0% epilactose, 87.5% lactulose, 0.1% galactose, 0.0% tagatose, 0.0% other monosaccharides) was concentrated to a solids content of 60 wt. %. In order to separate high-purity lactulose from the resulting concentrate by mutual separation of disaccharides, a separation operation was performed in Step 2 after the ionic form of the cation exchange resin as the packing in part of the packing bed units was changed to the Ca form. Specifically, a 1 N aqueous solution of calcium chloride, the amount of which was 44 L per packing bed unit, was flowed down through the packing bed units 2, 3, 7 and 8 to change the Na form of the packing to the Ca form. As a result, the constitution of the separator became such that 8 packing bed units 2, 3, 4, 5, 7, 8, 9 and 10 were packed with the packing in the Ca form while 2 packing bed units 1 and 6 were packed with the packing in the Na form. The resolution of lactulose and epilactose by used packing was 0.15 for the first packing in the Ca form and 0.08 for the second packing in the Na form, thus indicating better separation by the packing in the Ca form.

Other operating conditions were as follows:

Operating Temperature: 60° C.

One Cycle Time: 1.84 hr.

Linear Flow Velocity in Packing Bed Units between Starting Solution Inlet and Fraction C Withdrawal Outlet: 5.00 m/hr.

Feed Rate of Starting Solution: 1.76 L/hr. (0.012 L/L-packings/hr., based on packings)

Feed Rate of Eluent Water: 17.64 L/hr.

Withdrawal Rate of Fraction A: 9.11 L/hr.

Withdrawal Rate of Fraction C: 10.29 L/hr.

Eluent Water/Starting Solution (vol. ratio): 10.0

Open valves in each stage were the same as in Step 1, whereby fed liquids and withdrawn solutions were the same as in Step 1 (solutions were, of course, different in composition from those in Step 1).

As a result of operation, there were obtained fractions A and C having the following respective solids contents and solids-based compositions:

|  | Fraction A | Fraction C |
|---|---|---|
| Solids Content | 31 g/L | 104 g/L |
| Lactose | 31.2% | 0.0% |
| Epilactose | 23.3% | 1.6% |
| Lactulose | 45.5% | 98.3% |
| Galactose | 0.0% | 0.1% |
| Tagatose | 0.0% | 0.0% |
| Other Monosaccharides | 0.0% | 0.0% |

Incidentally, the lactulose recovery of the fraction C was 87.9%. The overall lactulose recovery based on the starting solution used in Step 1 was 78.5%. The total amount of eluent water used in Steps 1 and 2 was 18.9 times as much in volume as the starting solution used in Step 1.

In order to take Step 1 again, a 1 N aqueous solution of sodium chloride, the amount of which was 132 L per packing bed unit, was flowed down through the packing bed units 2, 3, 7 and 8 to change the Ca form of the packing to the Na form. As a result, the constitution of the separator became such that 4 packing bed units 4, 5, 9 and 10 were packed with the packing in the Ca form while 6 packing bed units 1, 2, 3, 6, 7 and 8 were packed with the packing in the Na form. When the foregoing separation operation in Step 1 was done again, substantially the same results were obtained.

Comparative Example 1

The fraction A solution (solids-based composition: 6.4% lactose, 6.0% epilactose, 87.5% lactulose, 0.1% galactose, 0.0% tagatose, 0.0% other monosaccharides) obtained in Step 1 in Example 1 was concentrated to a solids content of 60 wt. %. The separation operation in Step 2 was performed using the resulting concentrate as the starting solution with the same separator as in Step 1 in Example 1 in which separator the ionic form of packing in every packing bed unit was not changed but left intact. The operating conditions, of which only the one cycle time was varied, were as follows:

Operating Temperature: 60° C.

One Cycle Time: 1.77 hr.

Linear Flow Velocity in Packing Bed Units between Starting Solution Inlet and Fraction C Withdrawal Outlet: 5.00 m/hr.

Feed Rate of Starting Solution: 1.76 L/hr. (0.012 L/L-packings/hr., based on packings)

Feed Rate of Eluent Water: 17.64 L/hr.

Withdrawal Rate of Fraction A: 9.11 L/hr.

Withdrawal Rate of Fraction C: 10.29 L/hr.

Eluent Water/Starting Solution (vol. ratio): 10.0

Open valves in each stage as well as fed liquids and withdrawn solutions were the same as in Example 1.

As a result of operation, there were obtained fractions A and C having the following respective solids contents and solids-based compositions:

|  | Fraction A | Fraction C |
| --- | --- | --- |
| Solids Content | 46 g/L | 91 g/L |
| Lactose | 20.8% | 0.1% |
| Epilactose | 15.7% | 1.8% |
| Lactulose | 63.5% | 98.0% |
| Galactose | 0.0% | 0.1% |
| Tagatose | 0.0% | 0.0% |
| Other Monosaccharides | 0.0% | 0.0% |

Incidentally, the lactulose recovery of the fraction C was 76.6%. The overall lactulose recovery based on the starting solution used in Step 1 was 68.4%. The total amount of eluent water used in Steps 1 and 2 was 18.9 times as much in volume as the starting solution just like in Example 1.

Comparative Example 2

The same starting solution as used in Example 1 was subjected to separation with the separator, the constitution of which was such that 8 packing bed units were packed with the packing in the Ca form and 2 packing bed units were packed with the packing in Na form just like in Step 2 in Example 1, and which was used without a change in the ionic form of any packings in both Steps 1 and 2.

Specifically, the packings were Amberlite CG-6000 (gel type strongly acidic cation exchange resin for chromatographic separation) manufactured by Rohm and Haas Company. The total amount of the packings in the 10 packing bed units was 147 L. The packing bed units 1 and 6 were packed with the packing in the Na form, while the other packing bed units 2, 3, 4, 5, 7, 8, 9 and 10 were packed with the packing in the Ca form.

Other operating conditions in Step 1 were as follows:

Packing Bed Units: 108 mm in inner diameter, 1600 mm in bed height, 10 in the number of packed column units Operating Temperature: 60° C.

One Cycle Time: 1.90 hr.

Linear Flow Velocity in Packing Bed Units between Starting Solution Inlet and Fraction C Withdrawal Outlet: 5.00 m/hr.

Feed Rate of Starting Solution: 2.94 L/hr. (0.02 L/L-packings/hr., based on packings)

Feed Rate of Eluent Water: 20.58 L/hr.

Withdrawal Rate of Fraction A: 8.08 L/hr.

Withdrawal Rate of Fraction C: 15.44 L/hr.

Eluent Water/Starting Solution (vol. ratio): 7.0

Open valves in each stage were the same as in Example 1.

As a result of operation, there were obtained fractions A and C having the following respective solids contents and solids-based compositions:

|  | Fraction A | Fraction C |
| --- | --- | --- |
| Solids Content | 226 g/L | 31 g/L |
| Lactose | 6.4% | 0.9% |
| Epilactose | 6.1% | 0.3% |
| Lactulose | 87.4% | 45.1% |
| Galactose | 0.1% | 48.9% |
| Tagatose | 0.0% | 1.9% |
| Other Monosaccharides | 0.0% | 2.9% |

Incidentally, the lactulose recovery of the fraction A was 89.2%.

The fraction A solution (solids-based composition: 6.4% lactose, 6.1% epilactose, 87.4% lactulose, 0.1% galactose, 0.0% tagatose, 0.0% other monosaccharides) was concentrated to a solids content of 60 wt. %. The resulting concentrate was subjected to chromatographic separation in Step 2 with the same separator including the same packings as in Step 1 (8 packing bed units packed with the packing in the Ca form, and 2 packing bed units packed with the packing in the Na form).

Other operating conditions were as follows:

Operating Temperature: 60° C.

One Cycle Time: 1.84 hr.

Linear Flow Velocity in Packing Bed Units between Starting Solution Inlet and Fraction C Withdrawal Outlet: 5.00 m/hr.

Feed Rate of Starting Solution: 1.76 L/hr. (0.012 L/L-packings/hr., based on packings)

Feed Rate of Eluent Water: 17.64 L/hr.

Withdrawal Rate of Fraction A: 9.11 L/hr.

Withdrawal Rate of Fraction C: 10.29 L/hr.

Eluent Water/Starting Solution (vol. ratio): 10.0

Open valves in each stage as well as fed liquids and withdrawn solutions were the same as in Example 1.

As a result of operation, there were obtained fractions A and C having the following respective solids contents and solids-based compositions:

|  | Fraction A | Fraction C |
| --- | --- | --- |
| Solids Content | 31 g/L | 104 g/L |
| Lactose | 31.3% | 0.0% |
| Epilactose | 23.4% | 1.6% |
| Lactulose | 45.3% | 98.2% |
| Galactose | 0.0% | 0.2% |
| Tagatose | 0.0% | 0.0% |
| Other Monosaccharides | 0.0% | 0.0% |

Incidentally, the lactulose recovery of the fraction C was 87.9%. The overall lactulose recovery based on the starting solution used in Step 1 was 78.4%. The total amount of eluent water used in Steps 1 and 2 was 22.4 times as much in volume as the starting solution used in Step 1.

In comparison of Example 1 with Comparative Example 1, the lactulose purity and lactulose recovery of the fraction C in Step 2 in Example 1 were higher by 0.3% and by 11.3%, respectively, than those in Comparative Example 1, and the overall lactulose recovery in Steps 1 and 2 in Example 1 was higher by 10.1% than that in Comparative Example 1. In other words, in Example 1, the mutual separation of disaccharides was improved in Step 2 by increasing the amount of the packing in Ca form by 4 packing bed units to improve the lactulose recovery.

In comparison of Example 1 with Comparative Example 2, the respective solutions substantially equal to each other in lactulose purity and lactulose recovery were obtained in Step 1 despite such different operating 1conditions that the load (feed rate) of the starting solution in Example 1 was 1.4 times as much as that in Comparative Example 2, and that the amount of eluent water used in Example 1 was smaller by 5.7% than that in Comparative Example 2. Also as a whole, the amount of eluent water used based on the amount of the starting solution in Example 1 was smaller by 15.6% than that in comparative example 2. In other words, in Example 1, an increase in the amount of the packing in the Na form by 4 packing bed units in Step 1 in comparison with that in Comparative Example 2 improved the separation of disaccharides from monosaccharides, whereby the load (feed rate) of the starting solution could be increased while decreasing the amount of eluent water used.

Example 2

A solution (solids content: 60 wt. %; solids-based composition: 3.5% nonsaccharide compounds, 2.4% trisaccharides, 92.4% sucrose, 0.1% glucose, 0.6% fructose+inositol, 0.1% glycerol, 0.9% betaine) obtained by subjecting cut sugar beet to extraction, carbonation, filtration, softening, and concentration was subjected as the starting solution to Step 1 of a 3-component separation procedure for separating it into a fraction A enriched with nonsaccharide compounds+trisaccharides, a fraction B enriched with sucrose, and a fraction C enriched with glucose+fructose+inositol+glycerol+betaine with the separator of FIG. 2. Incidentally, the nonsaccharide compounds were mostly salts, and further included polymeric substances such as proteins and colored substances.

Amberlite CR-1320 (gel type strongly acidic cation exchange resin for chromatographic separation) manufactured by Rohm and Haas Company was used as chromatographic packing. The ionic form of the ion exchange resin was the Na form at the beginning of operation, but became the equilibrated ionic form with the ionic composition of the starting solution through repeated cycles of operation to be composed of 15% of the Ca form, 45% of the K form and 40% of the Na form. Although part of the ionic form became the Ca form as a bivalent ion form because of use of the incompletely softened solution, most of the ionic form became the K form and the Na form as monovalent ion forms. The total amount of the packing in the 10 packing bed units was 147L.

Other operating conditions were as follows:
Packing Bed Units: 108 mm in inner diameter, 1600 mm in bed height, 10 in the number of packed column units
Operating Temperature: 60° C.
One Cycle Time: 1.25 hr.
In Stage 1 of Step 1,
Time Required in Stage 1: 0.15 hr.
Feed Rate of Starting Solution: 31.67 L/hr. (0.2153 L/L-packing/hr., based on packing)
Feed Rate of Eluent Water: 76.40 L/hr.
Withdrawal Rate of Fraction A: 13.13 L/hr.
Withdrawal Rate of Fraction B: 94.93 L/hr.
In Stages 2 to 10 of Step 1,
Linear Flow Velocity in Packing Bed Units between Starting Solution Inlet and Fraction C Withdrawal Outlet: 7.00 m/hr.
Feed Rate of Eluent Water: 33.07 L/hr.
Withdrawal Rate of Fraction A: 13.32 L/hr.
Withdrawal Rate of Fraction C: 19.75 L/hr.
Eluent Water/Starting Solution (vol. ratio): 10.1
Open valves in each stage were as follows:

| | |
|---|---|
| Stage 1 | 6F, 1D, 8A, 5B (starting solution feed, eluent water feed, fraction A withdrawal, fraction B withdrawal) |
| Stage 2 | 2D, 9A, 3C, Z (eluent water feed, fraction A withdrawal, fraction C withdrawal) |
| Stage 3 | 3D, 10A, 4C, Z (eluent water feed, fraction A withdrawal, fraction C withdrawal) |
| Stage 4 | 4D, 1A, 5C, Z (eluent water feed, fraction A withdrawal, fraction C withdrawal) |
| Stage 5 | 5D, 2A, 6C, Z (eluent water feed, fraction A withdrawal, fraction C withdrawal) |
| Stage 6 | 6D, 3A, 7C, Z (eluent water feed, fraction A withdrawal, fraction C withdrawal) |
| Stage 7 | 7D, 4A, 8C, Z (eluent water feed, fraction A withdrawal, fraction C withdrawal) |
| Stage 8 | 8D, 5A, 9C, Z (eluent water feed, fraction A withdrawal, fraction C withdrawal) |
| Stage 9 | 9D, 6A, 10C, Z (eluent water feed, fraction A withdrawal, fraction C withdrawal) |
| Stage 10 | 10D, 7A, 1C, Z (eluent water feed, fraction A withdrawal, fraction C withdrawal) |

In Stage 1, the starting solution F was fed to the packing bed unit 6 via the starting solution feed valve 6F positioned on the downstream side of the closed shutoff valve Z while simultaneously feeding eluent water D via the eluent water feed valve 1D, whereby a fraction B was withdrawn via the withdrawal valve 5B positioned on the upstream side of the shutoff valve Z while withdrawing a fraction A via the withdrawal valve 8. By contrast, in Stages 2 to 10, with the shutoff valve Z being opened and the starting solution feed being stopped, feed of eluent water and withdrawal of fractions A and C were done while sequentially displacing the eluent water feed position and the fractions A and C withdrawal positions in the downstream direction. Thus, Stage 1 and Stages 2 to 10 may be considered separate steps. Since the ionic form of the ion exchanger as chromatographic packing was not changed in Step 1, however, Stage 1 and Stages 2 to 10 were regarded as substeps of Step 1.

As a result of operation, there were obtained fractions A, B and C having the following respective solids contents and solids-based compositions:

| | Fraction A | Fraction B | Fraction C |
|---|---|---|---|
| Solids Content | 11 g/L | 241 g/L | 3 g/L |
| Nonsaccharide Compds. | 67.6% | 0.1% | 1.3% |
| Trisaccharides | 24.8% | 1.2% | 0.0% |
| Sucrose | 6.6% | 98.7% | 9.0% |
| Glucose | 0.0% | 0.0% | 5.6% |
| Betaine | 0.3% | 0.0% | 47.4% |
| Fructose + inositol | 0.5% | 0.0% | 31.8% |
| Glycerol | 0.2% | 0.0% | 4.9% |

Incidentally, the sucrose recovery of the fraction B was 99.5%, and the betaine recovery of the fraction C was 95.6%.

The fraction C solution (solids-based composition: 1.3% nonsaccharide compounds, 0.0% trisaccharides, 9.0% sucrose, 5.6% glucose, 47.4% betaine, 31.8% fructose+inositol, 4.9% glycerol) was concentrated to a solids content of 60 wt. %. In order to separate betaine from the resulting concentrate, a simulated moving bed 2-component separation operation was performed in Step 2 after the ionic form of the packing in part of the packing bed units was changed. Specifically, a 1 N aqueous solution of calcium chloride, the amount of which was 44 L per packing bed unit, was flowed down through the packing bed units 2, 3, 7 and 8 to change the ionic form of the packing in those packing bed units to the Ca form. As a result, the constitution of the separator became such that 4 packing bed units 2, 3, 7 and 8 were packed with the packing in the Ca form while 6 packing bed units 1, 4, 5, 6, 9 and 10 were packed with the packing in the mixed ion form of Ca, K and Na.

Incidentally, the eluting order of components separated by the cation exchange resin in the mixed ion form, not yet changed in the ionic form, was nonsaccharide compounds, trisaccharides, sucrose, glucose, betaine, fructose+inositol, and glycerol. The resolution of glucose and betaine and the resolution of betaine and fructose+inositol were as low as 0.01 and 0.05, respectively. Thus, separation of glucose and betaine from each other in particular could not be expected.

By contrast, the eluting order of components separated by the cation exchange resin in the Ca form was nonsaccharide compounds, trisaccharides, sucrose, glucose, fructose+inositol, glycerol, and betaine. The resolution of glycerol and betaine was 0.9, whereby separation of the two components from each other could be expected by converting part of the packing into the Ca form.

Other operating conditions were as follows:

Operating Temperature: 80° C.

One Cycle Time: 2.46 hr.

Linear Flow Velocity in Packing Bed Units between Starting Solution Inlet and Fraction C Withdrawal Outlet: 5.00 m/hr.

Feed Rate of Starting Solution: 7.35 L/hr. (0.05 L/L-packings/hr., based on packings)

Feed Rate of Eluent Water: 33.81 L/hr.

Withdrawal Rate of Fraction A: 29.40 L/hr.

Withdrawal Rate of Fraction C: 11.76 L/hr.

Eluent Water/Starting Solution (vol. ratio): 4.6

Open valves in each stage of Step 2 were as follows: Fed liquids and withdrawn solutions were common to all stages. Specifically, the starting solution and eluent water were fed and 2 fractions A and C were withdrawn.

| Stage 1 | 6F, | 1D, | 8A, | 2C, | Z |
| Stage 2 | 7F, | 2D, | 9A, | 3C, | Z |
| Stage 3 | 8F, | 3D, | 10A, | 4C, | Z |
| Stage 4 | 9F, | 4D, | 1A, | 5C, | Z |
| Stage 5 | 10F, | 5D, | 2A, | 6C, | Z |
| Stage 6 | 1F, | 6D, | 3A, | 7C, | Z |
| Stage 7 | 2F, | 7D, | 4A, | 8C, | Z |
| Stage 8 | 3F, | 8D, | 5A, | 9C, | Z |
| Stage 9 | 4F, | 9D, | 6A, | 10C, | Z |
| Stage 10 | 5F, | 10D, | 7A, | 1C, | Z |

As a result of operation, there were obtained fractions A and C having the following respective solids contents and solids-based compositions:

|  | Fraction A | Fraction C |
| --- | --- | --- |
| Solids Content | 106 g/L | 220 g/L |
| Nonsaccharide Compds. | 2.4% | 0.1% |
| Trisaccharides | 0.0% | 0.0% |
| Sucrose | 16.5% | 0.0% |
| Glucose | 10.3% | 0.0% |
| Fructose + inositol | 58.9% | 0.0% |
| Glycerol | 8.9% | 0.2% |
| Betaine | 3.0% | 99.8% |

Incidentally, the betaine recovery of the fraction C was 96.1%.

In order to take Step 1 again, a 1 N aqueous solution of sodium chloride, the amount of which was 132 L per packing bed unit, was flowed down through the packing bed units 2, 3, 7 and 8 to convert the packing in those bed units into the Na form. When the foregoing separation operation in Step 1 was done again, the ionic form composition of the packing was equilibrated with that of the starting solution, and substantially the same results were obtained.

Comparative Example 3

The fraction C solution (solids-based composition: 1.3% nonsaccharide compounds, 0.0% trisaccharides, 9.0% sucrose, 5.6% glucose, 47.4% betaine, 31.8% fructose+inositol, 4.9% glycerol) obtained in Step 1 in Example 2 was concentrated to a solids content of 60 wt. %. In order to separate betaine from the resulting concentrate, a simulated moving bed 2-component separation operation was performed with the same separator as in Step 1 in Example 2 in which separator the ionic form of the packing in every packing bed unit was not changed but left intact. Having regard to the fact that the eluting order of components was nonsaccharide compounds, trisaccharides, sucrose, glucose, betaine, fructose+inositol, and glycerol, betaine was recovered in a fraction A under the following operating conditions:

The ionic form composition of the packing in every packing bed unit was equilibrated with the ionic form composition of the starting solution in Step 1 of Example 2, whereby the packing was the cation exchange resin still in the mixed ion form of 15% Ca, 45% K and 40% Na. The total amount of the packing in the 10 packing bed units was still 147 L.

Other operating conditions were as follows:

Packing Bed Units: 108 mm in inner diameter, 1600 mm in bed height, 10 in the number of packed column units Operating Temperature: 80° C.

One Cycle Time: 2.26 hr.

Linear Flow Velocity in Packing Bed Units between Starting Solution Inlet and Fraction C Withdrawal Outlet: 5.00 m/hr.

Feed Rate of Starting Solution: 1.18 L/hr. (0.008 L/L-packing/hr., based on packing)

Feed Rate of Eluent Water: 7.35 L/hr.

Withdrawal Rate of Fraction A: 4.12 L/hr.

Withdrawal Rate of Fraction C: 4.41 L/hr.

Eluent Water/Starting Solution (vol. ratio): 6.25

Open valves in each stage as well as fed liquids and withdrawn solutions were the same as in Step 2 in Example 2 (solutions were, of course, different in composition from those in Step 2 in Example 2).

As a result of operation, there were obtained fractions A and C having the following respective solids contents and solids-based compositions:

|  | Fraction A | Fraction C |
| --- | --- | --- |
| Solids Content | 125 g/L | 89 g/L |
| Nonsaccharide Compds. | 1.3% | 1.3% |
| Trisaccharides | 0.0% | 0.0% |
| Sucrose | 10.2% | 7.4% |
| Glucose | 8.5% | 1.8% |
| Betaine | 68.6% | 20.0% |
| Fructose + inositol | 11.1% | 58.4% |
| Glycerol | 0.2% | 11.1% |

Incidentally, the betaine recovery of the fraction C was 81.8%.

Comparison of Step 2 in Example 2 with Comparative Example 3 is as follows: The betaine purity and the betaine recovery in Step 2 in Example 2 were 99.8% and 96.1%, respectively, which were overwhelmingly superior to those in Comparative Example 3, wherein the betaine purity and the betaine recovery were 68.6% and 81.8%, respectively. Thus, it was understood that high-purity betaine can be recovered at a high recovery according to the present invention. In other words, separation of betaine was greatly improved by changing the ionic form of the packing in 4 packing bed units to the Ca form.

Comparative Example 4

When the same starting solution as subjected to Step 1 in Example 2 was subjected to Step 1 of separation operation with the separator which went through Step 2 in Example 2, Ca ions in the cation exchange resin as the packing were ion-exchanged by K ions and Na ions in the starting solution to dissolve into the liquid phase and react with carbonate ions, sulfate ions, etc. in the liquid phase, thereby forming an insoluble precipitate, part of which flowed out together with the withdrawn solutions. Accordingly, the separation operation was stopped in order to avoid occlusion of the separator. In other words, it was understood that, when Step 1 is started again with a separator which has gone through Step 2, the cation exchange resin, the ionic form of which has been changed to the Ca form, must be converted into such an ionic form as not to form a precipitate.

INDUSTRIAL APPLICABILITY

According to the chromatographic separation process of the present invention for separating a starting fluid material containing at least 3 components into at least 3 fractions through a plurality of steps with a chromatographic separator packed with an ion exchanger as at least part of chromatographic packing (sorbent), chromatographic separation is effected by changing at least part of the ionic form of part or the whole of the ion exchanger to a suitable ionic form high in the resolution of components to be separated (components desired to be separated) in each step, whereby there can be produced effects such as a decrease in the amount of desorbent (eluent) to be used, an increase in the purities of desired substances, and an increase in the recoveries of the desired substances. In the aforementioned conventional chromatographic separation methods, it is conceivable to use as eluent a mixed liquid of, e.g., ethanol and water, having a suitable composition, in order to decrease the amount of eluent to be used. However, this involves a problem of inapplicability to a case where eluent other than a single solvent such as water cannot be used as desorbent. By contrast, the process of the present invention can decrease the amount of desorbent to be used even if it is a single solvent.

One unit of the simulated moving bed chromatographic separator of the present invention can effectively be used in a plurality of chromatographic separation processes as substantiated by Example 2 wherein sucrose and betaine were each separated and purified with a high purity at a high recovery while using only one unit of the separator. Particularly in industrial fields such as the beet sugar industry wherein factories are intensively run only for 3 to 4 months in winter, for example, in Japan, one unit of the separator of the present invention can effectively be used for carrying out a variety of chromatographic separation processes to enable the unit to be used substantially fully throughout the year. This is of very great industrial significance.

What is claimed is:

1. A chromatographic separation process for separating a starting fluid material comprising at least three components into at least three fractions, said process comprising:
    a) providing a chromatographic separator comprising a plurality of packing beds packed with chromatographic packing, said chromatographic packing at least in part comprising ion exchanger, and in which chromatographic separator at least the position of feeding desorbent is intermittently displaced in the direction of fluid flow;
    b) separating said starting fluid material with said chromatographic separator to yield a plurality of fractions;
    c) manipulating the ion exchanger so as to change at least part (based on ion exchange capacity) of the ionic form of part of said ion exchanger to yield changed ion exchanger; and
    d) separating at least one of said fractions with said changed ion exchanger to yield a further plurality of fractions.

2. A chromatographic separation process as claimed in claim 1, characterized in that said ion exchanger is an ion exchange resin.

* * * * *

UNITED STATES PATENT AND TRADEMARK OFFICE
CERTIFICATE OF CORRECTION

PATENT NO. : 6,409,922 B1  
DATED : June 25, 2002  
INVENTOR(S) : Kikuzo Kaneko et al.

It is certified that error appears in the above-identified patent and that said Letters Patent is hereby corrected as shown below:

Column 3,  
Line 51, delete "is"

Column 4,  
Line 57, after "linked" insert a -- . -- (period)

Column 6,  
Line 54, after "ionic forms" delete "; A"

Column 8,  
Line 56, after "valve" delete "4"

Column 11,  
Line 45, change "rightupper" to -- right-upper --

Column 12,  
Line 26, change "a real" to -- areal --

Column 17,  
Line 4, change "lconditions" to -- conditions --

Signed and Sealed this

Ninth Day of September, 2003

JAMES E. ROGAN  
*Director of the United States Patent and Trademark Office*